US00PP26873P2

(12) United States Plant Patent
Meulenbroek

(10) Patent No.: US PP26,873 P2
(45) Date of Patent: Jun. 28, 2016

(54) STRAWBERRY PLANT NAMED 'VIVALDI'

(50) Latin Name: *Fragaria×ananassa*
Varietal Denomination: Vivaldi

(71) Applicant: Egbertus Joseph Meulenbroek, Zetten (NL)

(72) Inventor: Egbertus Joseph Meulenbroek, Zetten (NL)

(73) Assignee: Fresh Forward Holding B.V., Eck en Wiel (NL)

( * ) Notice: Subject to any disclaimer, the term of this patent is extended or adjusted under 35 U.S.C. 154(b) by 0 days.

(21) Appl. No.: 14/120,737

(22) Filed: Jun. 21, 2014

(51) Int. Cl.
*A01H 5/08* (2006.01)

(52) U.S. Cl.
USPC ..... Plt./208

(58) Field of Classification Search
USPC ..... Plt./208, 209
CPC ..... A01H 5/0893; A01H 5/08
See application file for complete search history.

(56) References Cited

PUBLICATIONS http://www.visionspictures.com/image/visi/visi128688; May 28, 2014, 1 page.*

* cited by examiner

*Primary Examiner* — Kent L Bell
(74) *Attorney, Agent, or Firm* — C. A. Whealy

(57) ABSTRACT

A new and distinct cultivar of Strawberry plant named 'Vivaldi', characterized by its compact and semi-upright plant habit; moderately vigorous to vigorous growth habit; uniform fruit ripening; medium-sized conical fruits that are glossy and bright red in color; pleasant fruit aroma and taste; excellent fruit postharvest longevity; and resistance to *Botrytis cinerea* and *Phytophthora cactorum.*

3 Drawing Sheets

Botanical designation: *Fragaria×ananassa.*
Cultivar denomination: 'VIVALDI'.

BACKGROUND OF THE INVENTION

The present Invention relates to a new and distinct cultivar of Strawberry plant, botanically known as *Fragaria×ananassa* and hereinafter referred to by the name 'Vivaldi'.

The new Strawberry plant is a product of a planned breeding program conducted by the Inventor in Elst, Gelderland, The Netherlands. The objective of the breeding program was to develop new early-ripening Strawberry plants with good fruit quality, ease of harvesting, good postharvest longevity and resistance to pathogens.

The new Strawberry plant originated from a cross-pollination made by the Inventor during the spring of 2003 of a proprietary Strawberry selection identified as code name E1993-053, not patented, as the female, or seed, parent with the Strawberry 'Sonata', disclosed in U.S. Plant Pat. No. 18,000, as the male, or pollen, parent. The new Strawberry plant was discovered and selected by the Inventor as a single plant from within the progeny of the stated cross-pollination in a controlled environment in Elst, Gelderland, The Netherlands during the summer of 2005.

Asexual reproduction of the new Strawberry plant by cuttings in a controlled environment at Elst, Gelderland, The Netherlands since the autumn of 2005, has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Vivaldi'. These characteristics in combination distinguish 'Vivaldi' as a new and distinct Strawberry plant:

1. Compact and semi-upright plant habit.
2. Moderately vigorous to vigorous growth habit.
3. Uniform fruit ripening.
4. Medium-sized conical fruits that are glossy and bright red in color.
5. Pleasant fruit aroma and taste.
6. Excellent fruit postharvest longevity.
7. Resistant to *Botrytis cinerea* and *Phytophthora cactorum.*

Plants of the new Strawberry differ from plants of the female parent selection in the following characteristics:

1. Fruits of plants of the new Strawberry are conical in shape whereas fruits of plants of the female parent selection are round in shape.
2. Plants of the new Strawberry and the female parent selection differ in fruit color as plants of the female parent selection have darker red-colored fruits.

Plants of the new Strawberry differ from plants of the male parent, 'Sonata', in the following characteristics:

1. Plants of the new Strawberry are more upright, more vigorous and larger than plants of 'Sonata'.
2. Plants of the new Strawberry have larger leaves with three leaflets per leaf whereas plants of 'Sonata' have three to five leaflets per leaf.

3. Plants of the new Strawberry flower later than plants of 'Sonata'.
4. Plants of the new Strawberry and 'Sonata' differ in fruit color as plants of 'Sonata' produce orange-colored fruits.
5. Fruits of plants of the new Strawberry are firmer than fruits of plants of 'Sonata'.

Plants of the new Strawberry can be compared to plants of Strawberry 'Holiday', not patented. In side-by-side comparisons, plants of the new Strawberry differed primarily from plants of 'Holiday' in fruit shape as fruits of plants of 'Holiday' were round.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a side perspective view of typical fruiting plants of 'Vivaldi' grown in a hydroponic system.

The photograph on the second sheet is a close-up view of typical developing and fully opened flowers of 'Vivaldi'.

The photograph on the third sheet is a close-up view of typical developing and developed fruits of 'Vivaldi'.

DETAILED BOTANICAL DESCRIPTION

The aforementioned photographs, following observations and measurements describe plants grown during the spring and summer in a glass-covered greenhouse in Eck en Wiel, The Netherlands and under cultural practices typical of commercial Strawberry production. During the production of the plants, day temperatures ranged from 12° C. to 23° C. and night temperatures ranged from 8° C. to 12° C. Plants were 2.5 months old when the photographs and description were taken. In the following description, color references are made to The Royal Horticultural Society Colour Chart, 2001 Edition, except where general terms of ordinary dictionary significance are used.

Botanical classification: *Fragaria×ananassa* 'Vivaldi'.

Parentage:

*Female, or seed, parent.*—Proprietary seedling selection of *Fragaria×ananassa* identified as code name E1993-053, not patented.

*Male, or pollen, parent.*—*Fragaria×ananassa* 'Sonata', disclosed in U.S. Plant Pat. No. 18,000.

Propagation:

*Type.*—By cuttings.

*Time to produce a rooted young plant, summer.*—About twelve days at soil temperatures ranging from 18° to 20° C.

*Root description.*—Medium in thickness, fibrous; creamy white to white in color.

*Rooting habit.*—Freely branching; medium density.

Plant description:

*Plant and growth habit.*—Perennial; compact and semi-upright plant habit; leaves basal; moderately vigorous to vigorous growth habit.

*Plant height.*—About 25 to 30 cm.

*Plant diameter.*—About 35 to 40 cm.

Leaf description:

*Arrangement.*—Basal rosette; compound with typically three leaflets per leaf.

*Leaflet length.*—About 9 to 12 cm.

*Leaflet width.*—About 8 to 11 cm.

*Leaflet shape.*—Broadly ovate.

*Leaflet apex.*—Obtuse to acute.

*Leaflet base.*—Obtuse to rounded.

*Leaflet margin.*—Serrated to lobed.

*Leaflet texture, upper surface.*—Pubescent.

*Leaflet texture, lower surface.*—Pubescent, rough.

*Leaflet venation.*—Pinnate.

*Leaflet color.*—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Petioles.*—Length: About 9 to 15 cm. Diameter: About 2.5 to 5 mm. Texture, upper and lower surfaces: Pubescent. Color, upper and lower surfaces: Close to 145A.

Flower description:

*Flower form and flowering habit.*—Rotate flowers arranged singly at lateral apices; flowers held at the foliar plane.

*Fragrance.*—None detected.

*Natural flowering season.*—Plants flower in April and May in The Netherlands.

*Flower diameter.*—About 2.5 to 3.5 cm.

*Flower depth (height).*—About 5 mm.

*Petals.*—Arrangement: Single whorl of six petals; petals imbricate. Length: About 8 mm to 12 mm. Width: About 8 mm to 12 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals.*—Arrangement and calyx description: Single whorl of eight to twelve sepals; calyx, star-shaped; sepals are orientated upwards from the fruit. Length: About 5 mm to 8 mm. Width: About 3 mm to 5 mm. Shape: Lanceolate to ovate. Apex: Acute. Base: Fused. Margin: Entire. Texture, upper and lower surfaces: Pubescent. Color, upper and lower surfaces: Close to 137A.

*Peduncles.*—Length: About 7 cm to 10 cm. Diameter: About 1 mm to 2 mm. Strength: Strong. Texture: Pubescent. Color: Close to 144B.

*Pedicels.*—Length: About 2 cm to 5 cm. Diameter: About 1 mm to 2 mm. Strength: Strong. Texture: Pubescent. Color: Close to 144B.

*Reproductive organs.*—Stamens: Quantity per flower: About 25. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruits: Postharvest longevity: Long, about ten days at temperatures about 7° C. Length: About 4 cm to 6 cm. Diameter: About 3 cm to 6 cm. Shape: Conical. Typical fruit weight per fruit: About 19.3 grams. Observed fruit weight per fruit: About 18.3 grams. Typical fruit weight per plant:

About 1,280 grams. Observed fruit weight per plant: About 1,145 grams. Firmness: Firm. Fragrance, taste: Pleasant; good balance between sweetness and acidity. Luster: Glossy. Surface unevenness: Absent or very weak. Color, surface: Close to 44A. Color, flesh: Close to 41A. Achene position: Slightly indented to indented. Achene color: At early fruiting stage, close to 1A; with maturity, color is closer to 41A and 42A.

Disease and pest resistance: Plants of the new Strawberry have been observed to be resistant to *Botrytis cinerea* and *Phytophthora cactorum*. Fruits of plants of the new Strawberry have been observed to be resistant to Mildew pathogens. Plants of the new Strawberry have not been observed to be resistant to pests and other pathogens common to Strawberry plants.

It is claimed:

1. A new and distinct Strawberry plant named 'Vivaldi' as illustrated and described.

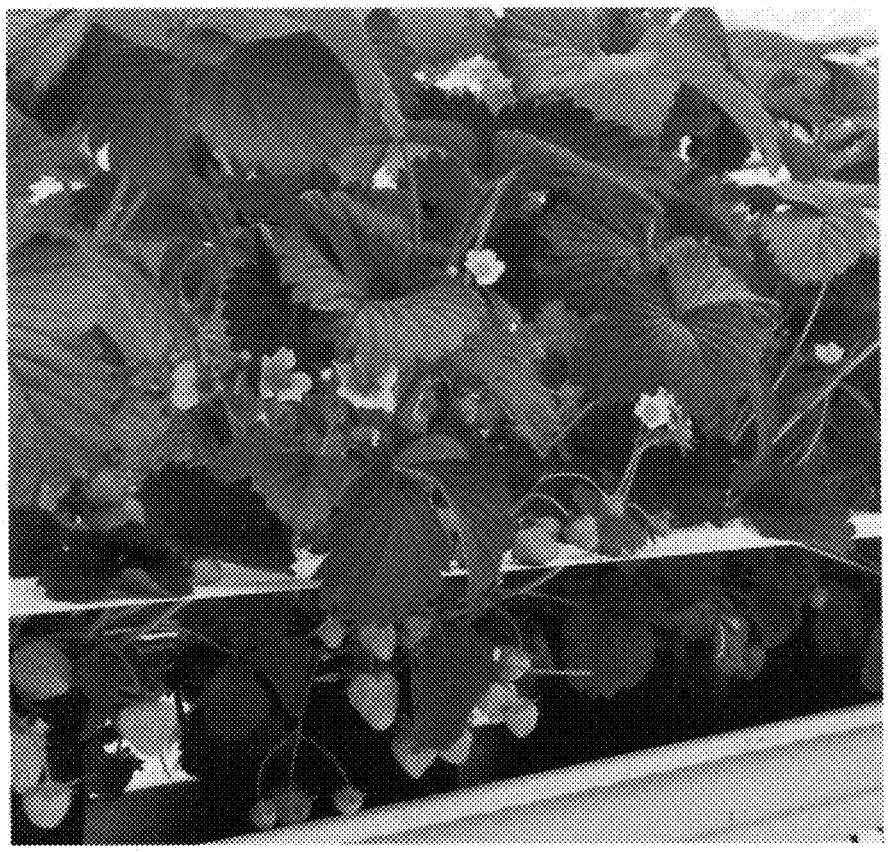

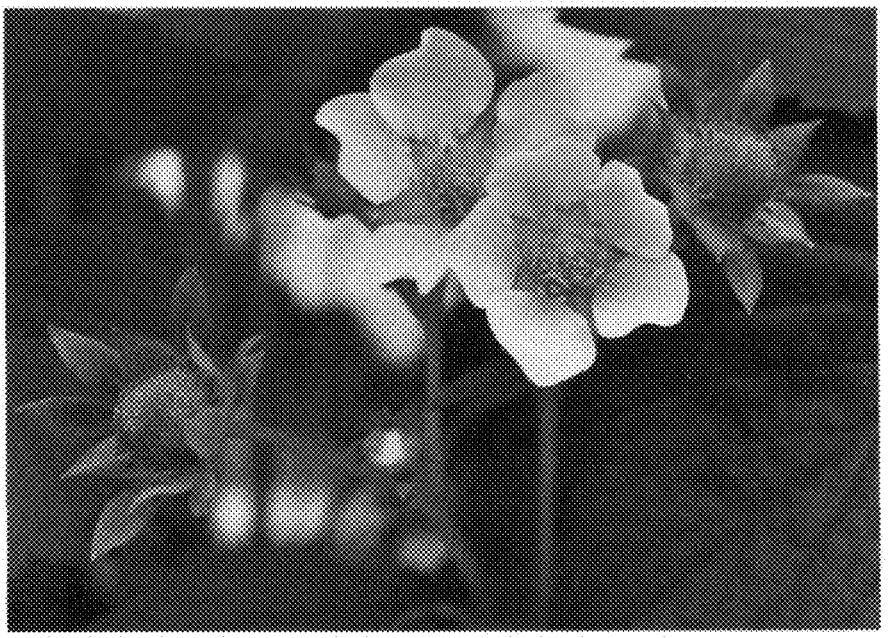

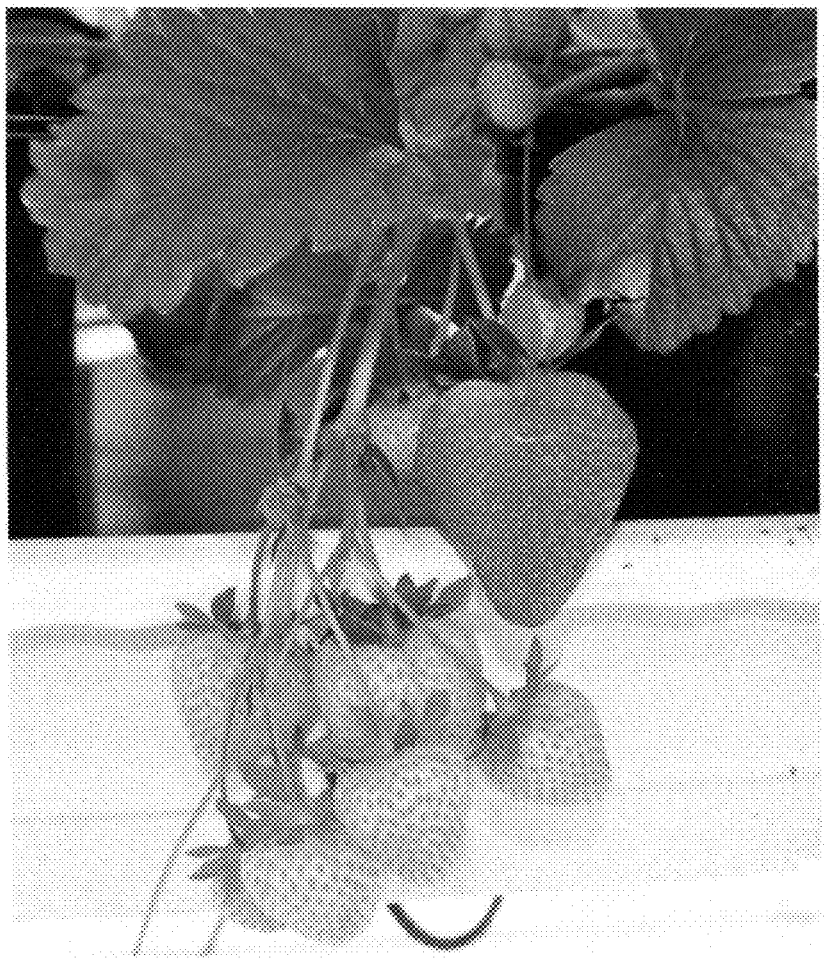

* * * * *